US012765778B2

(12) United States Patent
Olivo et al.

(10) Patent No.: US 12,765,778 B2
(45) Date of Patent: Oct. 20, 2026

(54) SYSTEM AND A METHOD TO DISTINGUISH BETWEEN BENIGN AND MALIGNANT BREAST TUMORS

(71) Applicants: Agency for Science, Technology and Research, Singapore (SG); National University Hospital (Singapore) Pte Ltd, Singapore (SG)

(72) Inventors: Malini Olivo, Singapore (SG); Yong Geng Goh, Singapore (SG); Ghayathri Balasundaram, Singapore (SG); Mohesh Moothanchery, Singapore (SG); Renzhe Bi, Singapore (SG); Ruochong Zhang, Singapore (SG)

(73) Assignees: Agency for Science, Technology and Research, Singapore (SG); National University Hospital (Singapore) Pte Ltd, Singapore (SG)

( * ) Notice: Subject to any disclaimer, the term of this patent is extended or adjusted under 35 U.S.C. 154(b) by 121 days.

(21) Appl. No.: 18/727,127

(22) PCT Filed: Jan. 4, 2023

(86) PCT No.: PCT/SG2023/050006
§ 371 (c)(1),
(2) Date: Jul. 8, 2024

(87) PCT Pub. No.: WO2023/132792
PCT Pub. Date: Jul. 13, 2023

(65) Prior Publication Data

US 2025/0098963 A1 Mar. 27, 2025

(30) Foreign Application Priority Data

Jan. 7, 2022 (SG) ............................ 10202200190S

(51) Int. Cl.
*A61B 5/00* (2006.01)
*G06T 7/00* (2017.01)
*G16H 30/20* (2018.01)

(52) U.S. Cl.
CPC .......... *A61B 5/0095* (2013.01); *G06T 7/0012* (2013.01); *G16H 30/20* (2018.01);
(Continued)

(58) Field of Classification Search
CPC ..... A61B 5/0095; A61B 5/145; A61B 8/0833; A61B 8/085; A61B 8/0858; A61B 8/0875;
(Continued)

(56) References Cited

U.S. PATENT DOCUMENTS 9,757,092 B2 9/2017 Oraevsky et al.
10,888,304 B2 1/2021 O'Donnell et al.
(Continued)

FOREIGN PATENT DOCUMENTS

CN 111407239 A 7/2020

OTHER PUBLICATIONS

Goh et al., "Multispectdral Optoacoustic Tomography in Assessment of Breast Tumor Margins During Breast-Conserving Surgery: A First-in-Human Case Study," Clinical Breast Cancer, 2018, pp. 1-4.
Alexander Graham Bell, "The Production of Sound by Radiant Energy," Science, May 28, 1881, vol. 2, No. 48, pp. 242-253.
Diot et al., "Multispectral Optoacoustic Tomography (MSOT) of Human Breast Cancer," Clinical Cancer Research, vol. 23, No. 22, Nov. 15, 2017, pp. 6912-6922.
(Continued)

*Primary Examiner* — Amal Aly Farag
(74) *Attorney, Agent, or Firm* — Shackelford, McKinley & Norton, LLP

(57) ABSTRACT

An ex vivo method and system of identifying a state of a tumor margin in a sample. An ultrasound image and a photoacoustic image are generated, where the system includes a probe configured to deliver a pulsed laser from a laser source to a sample, where the laser source is operable
(Continued)

to generate the pulsed laser. Furthermore, there are arrays coupled to the probe, where one of the arrays includes transducing elements arranged thereon which are operable to transmit and collect ultrasound signals, and where one of the arrays includes transducing elements arranged thereon which are operable to collect photoacoustic signals. Additionally, the system includes a data acquisition module which converts the ultrasound signals and the photoacoustic signals into the ultrasound image and the photoacoustic image, respectively.

20 Claims, 11 Drawing Sheets

(52) U.S. Cl.
CPC ............... *G06T 2207/10132* (2013.01); *G06T 2207/30068* (2013.01); *G06T 2207/30096* (2013.01)

(58) Field of Classification Search
CPC ................ A61B 8/5223; G06T 7/0012; G06T 2207/10132; G06T 2207/30068; G06T 2207/30096; G16H 30/20; G16H 40/63; G16H 30/40
See application file for complete search history.

(56) References Cited

U.S. PATENT DOCUMENTS

2007/0167836 A1* 7/2007 Scepanovic .......... A61B 5/4312 600/476
2015/0327772 A1* 11/2015 Baba .................... A61B 5/0095 600/407
2019/0117197 A1 4/2019 Cheng et al.
2019/0164286 A1* 5/2019 Hashizume ............. G06T 11/60
2020/0069275 A1 3/2020 Stavros
2020/0268253 A1 8/2020 Wang et al.

OTHER PUBLICATIONS

Brem et al., “Screening Breast Ultrasound: Past, Present, and Future” American Journal of Roentgenology, vol. 204, Feb. 2015, pp. 234-240.
Liu et al., “Development of a Handheld Volumetric Photacoustic Imaging System with a Central-Holed 2D Matrix Aperture,” IEEE Transactions on Bio-Medical Engineering, Sep. 2020, pp. 1-8.
Attia et al., “A Review of Clinical Photoacoustic Imaging: Current and Future Trends,” Photoacoustics, vol. 16, 2019, pp. 1-18.
Zhou et al., “Transcranial Volumetric Imaging Using a Conformal Ultrasound Patch,” Nature, vol. 629, May 23, 2024, pp. 810-818.
International Search Report for PCT/SG2023/050006, mailed on Aug. 16, 2023.
Balasundaram, G. et al., Optoacoustic characterization of breast conserving surgery specimens—A pilot study. Photoacoustics, Apr. 27, 2020, vol. 19, pp. 100164.
Goh, Y. et al., Ultrasound Guided Optoacoustic Tomography in Assessment of Tumor Margins for Lumpectomies. Translational Oncology, Feb. 1, 2020, vol. 13, No. 2, pp. 254-261.
Becker A. et al., Multispectral optoacoustic tomography of the human breast: characterisation of healthy tissue and malignant lesions using a hybrid ultrasound-optoacoustic approach. Eur Radiol, Aug. 7, 2017, vol. 28, pp. 602-609.
Butler, R. et al., Optoacoustic Breast Imaging: Imaging-Pathology Correlation of Optoacoustic Features in Benign and Malignant Breast Masses. American Journal of Roentgenology, Nov. 1, 2018, vol. 211, No. 5, pp. 1155-1170.
Xi, G. et al., Computer-assisted quantification of tumor-associated collagen signatures to improve the prognosis prediction of breast cancer. BMC Medicine, Nov. 18, 2021, vol. 19, No. 1, article No. 273.
Goh, Y. et al., Biochemical “decoding” of breast ultrasound images with optoacoustic tomography fusion: First-in-human display of lipid and collagen signals on breast ultrasound. Photoacoustics, Jun. 15, 2022, vol. 27, pp. 100377.

* cited by examiner

SYSTEM AND A METHOD TO DISTINGUISH BETWEEN BENIGN AND MALIGNANT BREAST TUMORS

CROSS-REFERENCE TO RELATED APPLICATION

This application claims the benefit of priority of Singapore Patent Application No. 10202200190S, filed 7 Jan. 2022, the content of it being hereby incorporated by reference in its entirety for all purposes.

TECHNICAL FIELD

The present disclosure relates to an ex vivo method for identifying a state of a tumor margin in a sample. The present disclosure also relates to a method for determining a state of a tumor. The present disclosure further relates to a system operable to carry out aforesaid methods.

BACKGROUND

Cancer, particularly breast cancer, appears to be one of the most commonly occurring cancer in women with about over 2 million new cases worldwide in 2018.

In cancer diagnosis, including breast cancer diagnosis, biopsy seems to be the gold standard to confirm the malignancy of a tumor. Radiologists tend to choose biopsy if they cannot conclude whether the tumor is benign or malignant from ultrasound images. However, more than 75% biopsy of breast cancer tend to turn out benign, which adds a lot of unnecessary workload to the hospital and extra cost for the patients. For example, in Singapore, each biopsy may be about SGD 1,000. Therefore, there seems to be a great demand for a system and method to screen out the benign tumors before the patients go for biopsy. This may help reduce the burden of a nation's healthcare system and benefit patients greatly.

Referring to breast cancer as an example, early stage breast cancers (stages I and II) tend to be managed using breast conserving surgery (BCS) followed by radiation therapy. Nevertheless, there is at least a 20% chance that these tumors are not completely excised in BCS due to the lack of rapid and accurate margin assessment tool. Histopathology analysis, which seems to have remained the gold standard till date for resection margin assessment in clinics, is a technique that unfortunately tends to involve cellular and molecular level analysis which may take up to 48 hours just for specimen fixation followed by several days of sectioning, staining and microscopic imaging to assess the involvement of margins. Hence, there appears to be a need for a rapid and accurate margin assessment tool to make sure the tumor margin is cleared so that the patient do not have to undergo repetitive operation.

There is thus a need to provide for a solution that addresses one or more of the limitations mentioned above. The solution should at least provide for a system and a method for identifying a state of a tumor.

SUMMARY

In a first aspect, there is provided for an ex vivo method of identifying a state of a tumor margin in a sample, the method comprising:

operating a system to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals; and a data acquisition module which converts the ultrasound signals and the photoacoustic signals into the ultrasound image and the photoacoustic image, respectively, identifying from the photoacoustic image the presence or absence of lipids and observing for a pattern and distribution of the lipids, identifying from the photoacoustic image the presence or absence of collagen and observing for a pattern and distribution of the collagen;

identifying from the photoacoustic image the presence or absence of hemoglobin and observing for a pattern and distribution of the hemoglobin; and comparing from the photoacoustic image an intensity of the collagen and/or hemoglobin, if present, with an intensity of tissue proximal to the collagen and/or hemoglobin.

In another aspect, there is provided for a method of determining a state of a tumor, the method comprising:

operating a system to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals; and a data acquisition module which converts the ultrasound signals and the photoacoustic signals into the ultrasound image and the photoacoustic image, respectively, identifying from the ultrasound image the presence or absence of an abnormal tissue or a lesion;

identifying from the photoacoustic image the presence or absence of lipids and observing for a pattern and distribution of the lipids, identifying from the photoacoustic image the presence or absence of water and observing for a pattern and distribution of the water;

identifying from the photoacoustic image the presence or absence of collagen and observing for a pattern and distribution of the collagen;

identifying from the photoacoustic image the presence or absence of hemoglobin; and and observing for a pattern and distribution of the hemoglobin comparing from the photoacoustic image an intensity of the collagen and/or hemoglobin, if present, with an intensity of tissue proximal to the collagen and/or hemoglobin.

In another aspect, there is provided for a system operable to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals; and a data acquisition module which converts the ultrasound signals and the photoacoustic signals into the ultrasound image and the photoacoustic image, respectively.

BRIEF DESCRIPTION OF THE DRAWINGS

The drawings are not necessarily to scale, emphasis instead generally being placed upon illustrating the principles of the present disclosure. In the following description, various embodiments of the present disclosure are described with reference to the following drawings, in which:

FIG. 4C shows a two dimensional (2D) ultrasound image of the excised tissue demonstrating expected heterogeneity of the breast tissue. US in this instance denotes the range for the degree of shading obtained via ultrasound imaging. Scale bar denotes for 5 mm.

FIG. 4D shows photoacoustic images of the excised tissue indicating collagen (bold arrow) and lipid (dotted arrow) distribution which correlates well with histopathology. Scale bar denotes for 5 mm.

FIG. 5C shows a two dimensional (2D) ultrasound image of the excised tissue demonstrating expected heterogeneity of the breast tissue. US in this instance denotes the range for the degree of shading obtained via ultrasound imaging. Scale bar denotes for 5 mm.

FIG. 5D shows photoacoustic images of the excised tissue indicating collagen (bold arrow) and lipid (dotted arrow) distribution which correlates well with histopathology. Scale bar denotes for 5 mm.

FIG. 6C shows a two dimensional (2D) ultrasound image of the excised tissue demonstrating expected heterogeneity of the breast tissue. US in this instance denotes the range for the degree of shading obtained via ultrasound imaging. Scale bar denotes for 5 mm.

FIG. 6D shows photoacoustic images of the excised tissue indicating collagen (bold arrow) and lipid (dotted arrow) distribution which correlates well with histopathology. Scale bar denotes for 5 mm.

DETAILED DESCRIPTION

Figure 1A:
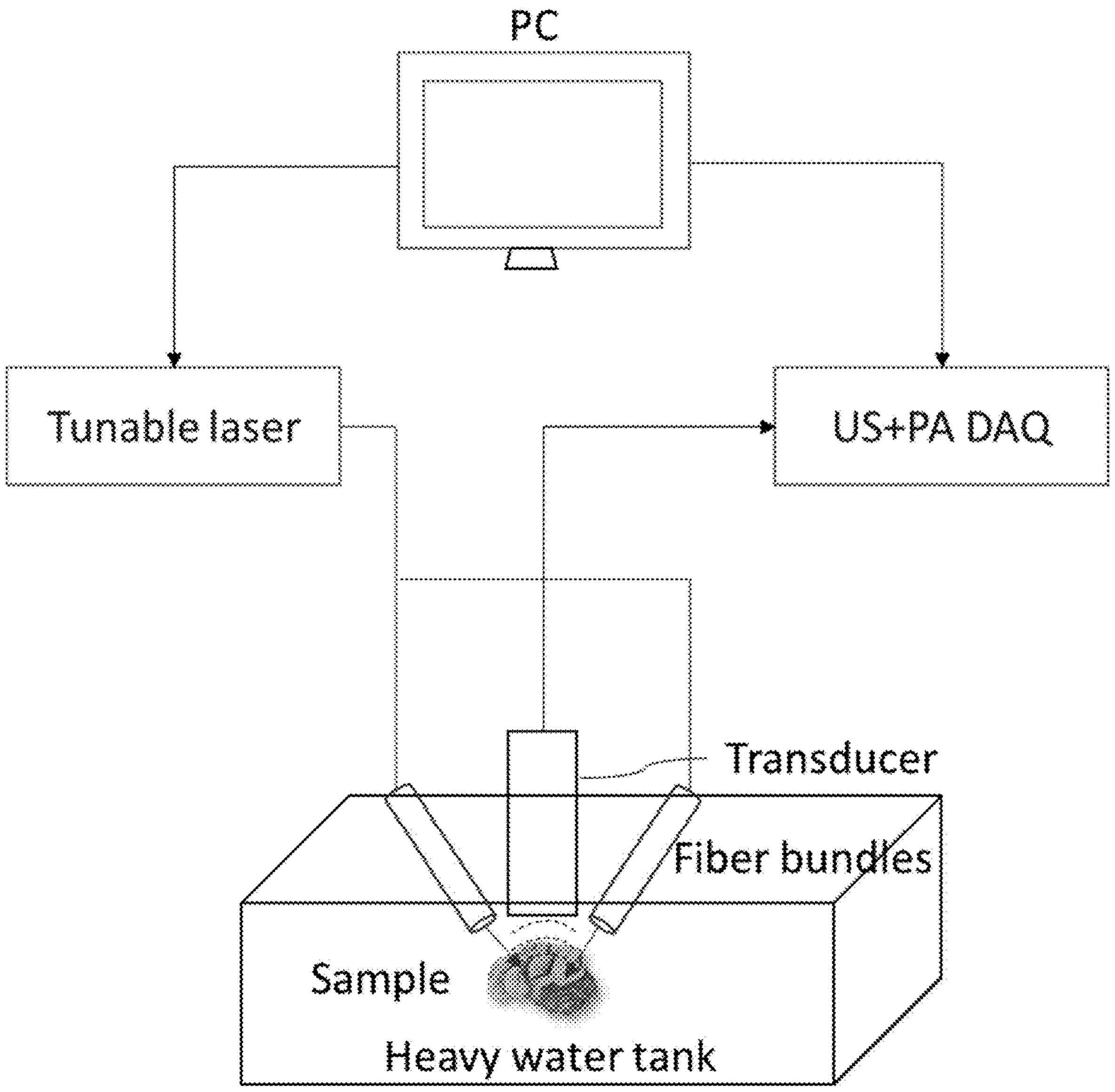
FIG. 1A is a general schematic of the present system, showing the ultrasound-photoacoustic (US-PA) dual frequency probe placed in heavy water tank for ex vivo tumor margin detection. US and PA denote for ultrasound and photoacoustic, respectively. PC and DAQ denote for a computer and the data acquisition module, respectively.
Figure 1B:
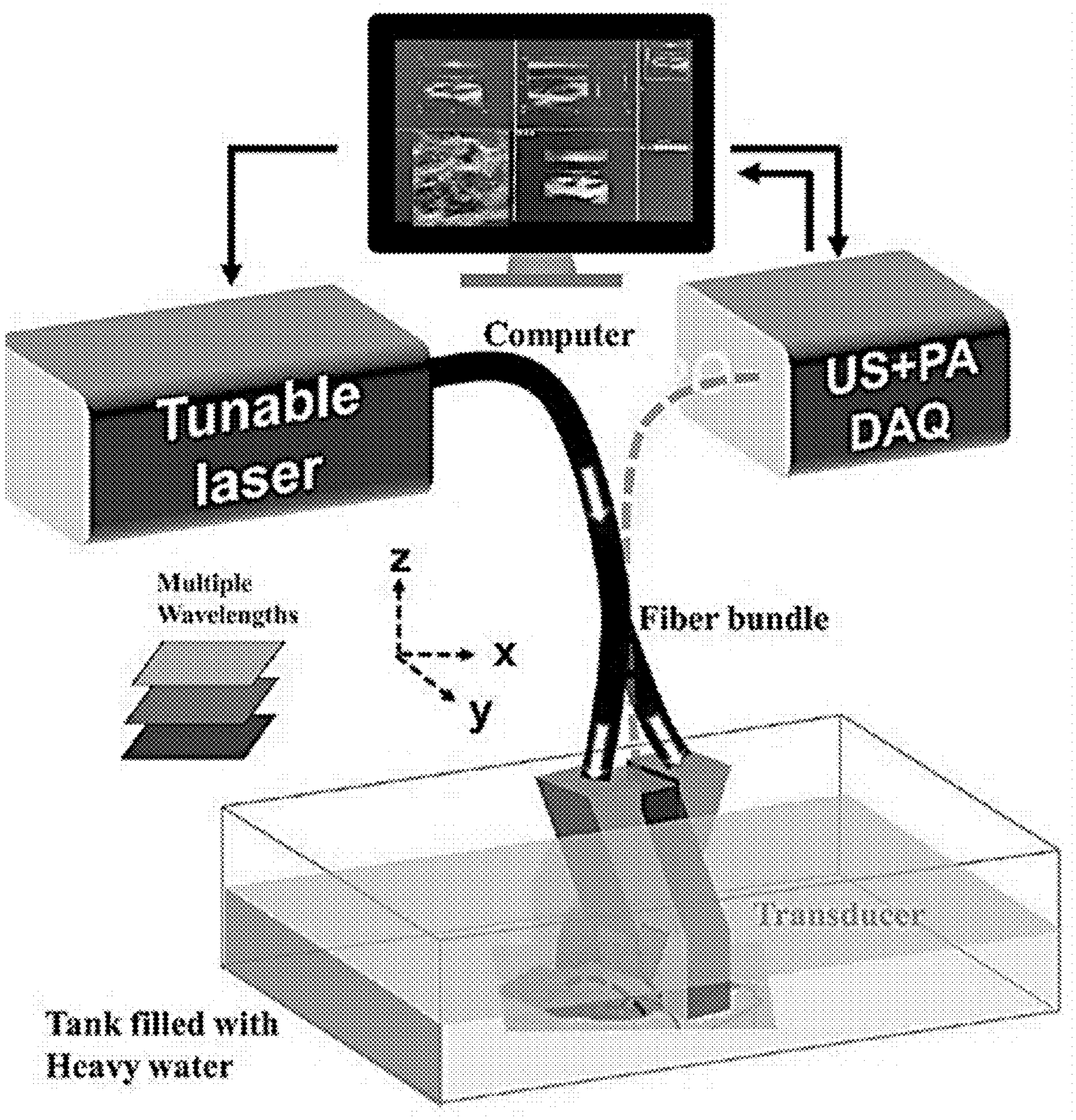
FIG. 1B is a general schematic of the present system, showing the ultrasound-photoacoustic (US-PA) dual frequency probe placed in heavy water tank for ex vivo tumor margin detection. US and PA denote for ultrasound and photoacoustic, respectively. DAQ denotes for the data acquisition module.

The following detailed description refers to the accompanying drawings that show, by way of illustration, specific details and embodiments in which the present disclosure may be practised.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

The present disclosure relates to an ex vivo method of identifying a state of a tumor margin in a sample (e.g. ex vivo tissue sample) and a method of determining a state of a tumor. The method of determining a state of a tumor can be an ex vivo method, as an ex vivo tissue sample can be used. The present disclosure also relates to a method for diagnosis of benign, indeterminate and malignant tumors.

The methods may involve a system operable to determine the state of the tumor and/or the state of the tumor margin. The system may include a probe configured to deliver a pulsed laser from a laser source to a sample. The laser source is operable to generate the pulsed laser. The system may include arrays coupled to the probe. In certain non-limiting embodiments, one of the arrays may include a planar surface having transducing elements arranged thereon which are operable to transmit and collect ultrasound signals and/or photoacoustic signals. In certain non-limiting embodiments, one of the arrays may include a curved surface having transducing elements arranged thereon which are operable to transmit and collect ultrasound signals and/or photoacoustic signals. In certain non-limiting embodiments, there may be one array having transducing elements arranged on the planar surface and one array having transducing elements arranged on the curved surface to transmit and collect ultrasound signals and/or photoacoustic signals. The system may include a data acquisition module which converts the ultrasound signals and the photoacoustic signals into an ultrasound image and a photoacoustic image, respectively, wherein the presence or absence of lipids, collagen, water and/or hemoglobin is identifiable from the photoacoustic image, and/or observing for a pattern and distribution of the lipids, collagen, water, and/or hemoglobin from the photoacoustic image.

Advantageously, the present methods and system afford co-registered histology image, ultrasound image, photoacoustic images (from which lipid, collagen and/or haemoglobin may be identified) to discover the relationship. Traditionally, clinicians and radiologists may not have access to photoacoustic images, and researchers may not have enough clinical knowledge to interpret the clinical images. Due to this, most researchers focused on improving the sensitivity of the breast tumor detection but ignored the specificity to the malignant tumor. Also, clinicians still require biopsy to confirm the malignancy. This gives rise to a painful point in that unnecessary biopsies continue to be carried out, which seems to remain ignored by researchers.

The present methods and system may provide an opportunity for an experienced radiologist to learn about photoacoustic imaging, which most radiologists do not have access to and combine it with ultrasound imaging.

Details of various embodiments of the present methods and system and advantages associated with the various embodiments are now described below. Where the embodiments and/or advantages are already described in the examples section herein further below, they shall not be iterated for brevity.

In the present disclosure, there is provided an ex vivo method of identifying a state of a tumor margin in a sample. The method may comprise operating a system to generate an ultrasound image and a photoacoustic image. The system may comprise a probe configured to deliver a pulsed laser from a laser source to a sample, wherein the laser source is operable to generate the pulsed laser. In various non-limiting embodiments, the probe may be movable. The system may comprise arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals. The system may comprise a data acquisition module which converts the ultrasound signals and the photoacoustic signals into the ultrasound image and the photoacoustic image, respectively.

The method may comprise identifying from the photoacoustic image the presence or absence of lipids and/or observing for a pattern and distribution of the lipids, identifying from the photoacoustic image the presence or absence of collagen and/or observing for a pattern and distribution of the collagen, identifying from the photoacoustic image the presence or absence of hemoglobin and/or observing for a pattern and distribution of the hemoglobin, and comparing from the photoacoustic image an intensity of the collagen and/or hemoglobin, if present, with an intensity of tissue proximal to the collagen and/or hemoglobin.

In various embodiments, the state of the tumor margin is negative, positive, or may comprise a dye.

The method involves use of laser for identifying a state of a tumor and/or a tumor margin. Laser may be directed onto a sample. The laser may be a pulsed laser. The sample absorbs light energy from the laser (e.g. pulsed laser), which then gets converted into sound energy through a "photoacoustic effect". For example, the photoacoustic effect may include formation of sound waves from the light absorption in a material, wherein the light intensity is varied, either periodically (modulated light) or as a single flash (pulsed light), to obtain such photoacoustic effect. Then, the sound (e.g. ultrasound) signal from the sample may be detected by ultrasound transducing elements. In various embodiments, operating the system may comprise operating the laser source to generate the pulsed laser having a wavelength ranging from 600 nm to 2000 nm (e.g. 600 nm to 1000 nm, 600 nm to 1500 nm, 1000 nm to 2000 nm, 1500 nm to 2000 nm, 1000 nm to 1500 nm), a wave period of 10 ns or less (e.g. 9 ns or less, 8 ns or less, 7 ns or less, 6 ns or less, 5 ns or less, 4 ns or less, 3 ns or less, 2 ns or less, 1 ns or less), and/or a frequency of 1 to 100 Hz (e.g. 10 to 100 Hz, 20 to 100 Hz, 30 to 100 Hz, 40 to 100 Hz, 50 to 100 Hz, 60 to 100 Hz, 70 to 100 Hz, 80 to 100 Hz, 90 to 100 Hz).

In various embodiments, operating the system may comprise having the laser source configured at an angle to the probe to deliver the pulsed laser to the sample, or having the laser source deliver the pulsed laser to the sample via a fiber, wherein one end of the fiber is configured at an angle to the probe.

In various embodiments, operating the system may comprise operating the probe in heavy water or having the probe incorporated with heavy water. For example, the probe can be immersed in a water tank with an optical window sealed by a thin transparent film. The optical window can be transparent. The probe can also be wrapped with a water bag. In various embodiments, "heavy water" refers to $D_2O$.

In various embodiments, the arrays may comprise one array having a planar surface configured between and adjacent to two arrays each having a curved surface. In certain non-limiting embodiments, operating the system may comprise operating transducing elements arranged on the planar surface at a higher frequency than or same frequency as the transducing elements arranged on the curved surface.

In various embodiments, observing for the pattern and distribution of the collagen may further comprise observing the thickness of the collagen.

In various embodiments, the method may further comprise observing the presence or absence of vascularity extension from a tumor. In various embodiments, the method may further comprise observing for heterogeneity of the issue from the ultrasound image. In various embodiments, the method may further comprise correlating the ultrasound image and the photoacoustic image to a histopathological microscopic image.

The present disclosure also provides for a method of determining a state of a tumor. Embodiments and advantages described for the method of the first aspect can be analogously valid for the present method subsequently described herein, and vice versa. Where the various embodiments and advantages have already been described above and in the examples section herein, they shall not be iterated for brevity.

The method may comprise operating a system to generate an ultrasound image and a photoacoustic image. The system may comprise a probe configured to deliver a pulsed laser from a laser source to a sample, wherein the laser source is operable to generate the pulsed laser. In various non-limiting embodiments, the probe may be movable. The system may comprise arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals. The system may comprise a data acquisition module which converts the ultrasound signals and the photoacoustic signals into the ultrasound image and the photoacoustic image, respectively.

The method may comprise identifying from the ultrasound image the presence or absence of an abnormal tissue or a lesion, identifying from the photoacoustic image the presence or absence of lipids and/or observing for a pattern and distribution of the lipids, identifying from the photoacoustic image the presence or absence of water and/or observing for a pattern and distrbution of the water, identifying from the photoacoustic image the presence or absence of collagen and/or observing for a pattern and distribution of the collagen, identifying from the photoacoustic image the presence or absence of hemoglobin and/or observing of a pattern and distribution of the hemoglobin, and comparing from the photoacoustic image an intensity of the collagen and/or hemoglobin, if present, with an intensity of tissue proximal to the collagen and/or hemoglobin.

In various embodiments, the state of the tumor is benign, malignant, or indeterminate. In various embodiments, the tumor is a breast cancer tumor.

The method involves use of laser for identifying a state of a tumor and/or a tumor margin. Laser may be directed onto a sample. The laser may be a pulsed laser. The sample absorbs light energy from the laser (e.g. pulsed laser), which then gets converted into sound energy through a "photoacoustic effect". For example, the photoacoustic effect may include formation of sound waves from the light absorption in a material, wherein the light intensity is varied, either periodically (modulated light) or as a single flash (pulsed light), to obtain such photoacoustic effect. Then, the sound (e.g. ultrasound) signal from the sample may be detected by ultrasound transducing elements. In various embodiments, operating the system may comprise operating the laser source to generate the pulsed laser having a wavelength ranging from 600 nm to 2000 nm (e.g. 600 nm to 1000 nm, 600 nm to 1500 nm, 1000 nm to 2000 nm, 1500 nm to 2000 nm, 1000 nm to 1500 nm), a wave period of 10 ns or less (e.g. 9 ns or less, 8 ns or less, 7 ns or less, 6 ns or less, 5 ns or less, 4 ns or less, 3 ns or less, 2 ns or less, 1 ns or less), and/or a frequency of 1 to 100 Hz (e.g. 10 to 100 Hz, 20 to 100 Hz, 30 to 100 Hz, 40 to 100 Hz, 50 to 100 Hz, 60 to 100 Hz, 70 to 100 Hz, 80 to 100 Hz, 90 to 100 Hz).

In various embodiments, operating the system may comprise having the laser source configured at an angle to the probe to deliver the pulsed laser to the sample, or having the laser source deliver the pulsed laser to the sample via a fiber, wherein one end of the fiber is configured at an angle to the probe.

In various embodiments, operating the system may comprise operating the probe in heavy water or having the probe incorporated with heavy water. For example, the probe can be immersed in water tank with an optical window sealed by a thin transparent film. The optical window can be transparent. The probe can also be wrapped with a water bag. In various embodiments, "heavy water" refers to $D_2O$.

In various embodiments, the arrays may comprise one array having a planar surface configured between and adjacent to two arrays each having a curved surface. In certain non-limiting embodiments, operating the system may comprise operating transducing elements arranged on the planar surface at a higher frequency than or same frequency as transducing elements arranged on the curved surface.

In various embodiments, the method may further comprise observing for heterogeneity of the issue from the ultrasound image. In various embodiments, the method may further comprise correlating the ultrasound image and the photoacoustic image to a histopathological microscopic image.

The present disclosure further provides for a system operable to generate an ultrasound image and a photoacoustic image. Embodiments and advantages described for aforesaid methods can be analogously valid for the present system subsequently described herein, and vice versa. Where the various embodiments and advantages have already been described above and in the examples section herein, they shall not be iterated for brevity.

The system may comprise a probe configured to deliver a pulsed laser from a laser source to a sample, wherein the laser source is operable to generate the pulsed laser. In various non-limiting embodiments, the probe is movable. The system may comprise arrays coupled to the probe, wherein one of the arrays comprises transducing elements arranged thereon which are operable to transmit and collect ultrasound signals, and wherein one of the arrays comprises transducing elements arranged thereon which are operable to collect photoacoustic signals. The system may comprise a data acquisition module which converts the ultrasound signals and the photoacoustic signals into the ultrasound image and the photoacoustic image, respectively.

The system includes a laser source for identifying a state of a tumor and/or a tumor margin. Laser may be directed from the laser source onto a sample. The laser may be a pulsed laser. The sample absorbs light energy from the laser (e.g. pulsed laser), which then gets converted into sound energy through a "photoacoustic effect". For example, the photoacoustic effect may include formation of sound waves from the light absorption in a material, wherein the light intensity is varied, either periodically (modulated light) or as a single flash (pulsed light), to obtain such photoacoustic effect. Then, the sound (e.g. ultrasound) signal from the sample may be detected by ultrasound transducing elements. In various embodiments, the laser source is operable to generate the pulsed laser having a wavelength ranging from 600 nm to 2000 nm, a wave period of 10 ns or less, and/or a frequency of 1 to 100 Hz. Other ranges of the wavelength, wave period, and frequency, are already described above and shall not be iterated for brevity.

In various embodiments, the laser source may be configured at an angle to the probe to deliver the pulsed laser to the sample, or the laser source delivers the pulsed laser to the sample via a fiber, wherein one end of the fiber is configured at an angle to the probe.

In various embodiments, the probe may be operable in heavy water or incorporated with heavy water. For example, the probe can be immersed in water tank with an optical window sealed by a thin transparent film. The optical window can be transparent. The probe can also be wrapped with a water bag. In various embodiments, "heavy water" refers to $D_2O$.

In various embodiments, the arrays may comprise one array having a planar surface configured between and adjacent to two arrays each having a curved surface.

In various embodiments, the transducing elements are arranged on the planar surface are operable at a higher frequency than or same frequency as the transducing elements arranged on the curved surface.

The word "substantially" does not exclude "completely" e.g. a composition which is "substantially free" from Y may be completely free from Y. Where necessary, the word "substantially" may be omitted from the definition of the present disclosure.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

Unless specified otherwise, the terms "comprising" and "comprise", and grammatical variants thereof, are intended to represent "open" or "inclusive" language such that they include recited elements but also permit inclusion of additional, unrecited elements.

EXAMPLES

The present disclosure relates to an ex vivo method for identifying a state of a tumor margin in a sample and a method for determining a state of a tumor. Both methods involve a system operable to generate an ultrasound image and a photoacoustic image.

In general, the system includes a hybrid ultrasound and photoacoustic (PA) imaging module. The system is operable for a method for an in vivo diagnosis of benign, indeterminate and malignant breast tumors, and operable to precisely assess the surgical tumor margins in ex vivo tissues. The in vivo diagnosis and tumor margin assessment is based on the images acquired from the hybrid ultrasound and PA imaging module and a software developed for auto diagnosis of aforesaid tumors. The diagnosis can involve interpretation of both high-resolution ultrasound and photoacoustic images from which, for example, lipid, collagen and haemoglobin, can be identified. From the acquisition of the ultrasound and photoacoustic images, clinicians can go through the diagnosis chart to distinguish whether there is positive or negative margin in the ex vivo samples and classify a tumor as benign or malignant for in vivo with high accuracy. The hybrid system of the present disclosure (which involves ultrasound and photoacoustic imaging) affords high-resolution capability for ultrasound to track smaller tumours and deeper imaging capability from the utilization of photoacoustic. Also, the present system involves a combination of high frequency transducer elements along with low frequency transducer elements within the same probe. An automated software is developed to assist the diagnosis based on the images.

The present methods and system are described in further details, by way of non-limiting examples, as set forth below.

Example 1: Description of One Non-Limiting Example of the Present System

The present system, which may be referred to as an imaging system, includes a hybrid probe for ultrasound and photoacoustic (PA) imaging, a pulsed laser source for photoacoustic stimulation, a ultrasound and PA data acquisition module (US+PA DAQ) which aids in generating ultrasound and/or ultrasound signal. The US+PA DAQ is also operable to receive ultrasound and PA signals. The system also includes a computer operable to control aforesaid components.

To generate the photoacoustic images, illumination on the sample was required. The illumination was provided by operating a laser source to direct a pulsed laser at a sample. In one non-limiting example, the illumination (i.e. laser) was provided through a fiber bundle (see FIG. 1A to 1B and FIG. 7A to 7B) from a high-speed wavelength-tunable laser source. The laser source is operable to generate a pulsed laser having a wavelength in the range of 600 nm to 2000 nm (e.g. 660 nm to 1300 nm or other ranges as described above), with a duration (i.e. period of wave) of 10 ns or less (or other ranges as described above), and a 1 Hz to 100 Hz (e.g. 5 Hz to 15 Hz, 10 Hz, or other ranges as described above) repetition rate.

The fiber bundle (can contain one or more fibers) output was attached to the probe at a specific angle. This is described in more detail in example 3 below.

The probe (and/or with the laser source for light illumination) was configured to a computer-controlled stage and is movable across the sample placed in an imaging chamber with heavy water (see FIGS. 1A and 1B) to enhance acoustic coupling. The scanner (i.e. probe) aids in providing cross-sectional 2D photoacoustic images with an user defined effective field-of-view (FOV) of about 20 mm to about 40 mm. Photoacoustic images were acquired at multiple wavelengths (e.g. 680 nm, 700 nm, 730 nm, 760 nm, 800 nm, 850 nm, 920 nm, 930 nm, 970 nm, 1000 nm, 1064 nm and 1100 nm). Multiple 2D images were captured and analysed one by one to visualise the tumor margin. The imaging speed depends on the laser source's switching speed. The laser source can have a per pulse wavlength switching speed. Both X (15 cm) and Y axis (5 cm) stages allow sufficient movement to scan small and bigger samples. That is to say, the probe (e.g. mounted on a motor stage) can move in a left-right direction (along X axis) and front-back direction (Y axis) along a 2D plane to scan at different positions of a sample. Z axis (vertical direction) is used only (but not limited to) for probe alignment to focus. In various non-limiting examples, the sample can be attached to a rotatable stage to flip the sample without needing human intervention for the flipping.

The probe may be referred to as a transducer probe, as the probe contains or is coupled to transducing elements. Transducing elements of the present disclosure are operable to aid in converting one form of energy into another, for example, the transducing elements are operable to aid in converting a signal in one form of energy to a signal in another form of energy. In various non-limiting examples, the ultrasound transducing elements are able to convert ultrasound received into ultrasound signals or vice versa. In various non-limiting examples, the photoacoustic transducing elements are able to convert light into photoacoustic signals. In non-limiting instances, the transducing elements for ultrasound imaging may operably emit ultrasound and receive ultrasound, while for photoacoustic imaging, the transducing elements may only receive ultrasound signals generated by the pulsed laser but may not emit ultrasound.

Through the present system and methods, ultrasound imaging can be carried out using a high frequency transducer (e.g. 7 MHz to 10 MHz) and photoacoustic imaging can be carried out using (i) transducer elements operable at a high frequency (e.g. 7 MHz to 10 MHz) and a lower frequency (e.g. 2 MHz to 5 MHz) or (ii) two sets of transducer elements one being a high frequency type (e.g. 7 MHz to 10 MHz) and the other a lower frequency type (e.g. 2 MHz to 5 MHz). The transducer elements can involve, for example, 64 to 512 (e.g. 128 to 256) transducing elements. The transducing elements can be arranged, for example, in any array. The transducing elements can be aligned either in a curved, a linear, or by a combination of curved and linear geometrical arrangement. That is to say, the tranducing elements can be geometrically arranged on a planar surface, a curved surface, or a combination of both.

In certain non-limiting examples, a dual frequency approach using (i) a linear array at high frequency for ultrasound imaging and (ii) a combination of two curved arrays and one linear array for photoacoustic imaging was carried out.

Figure 2:
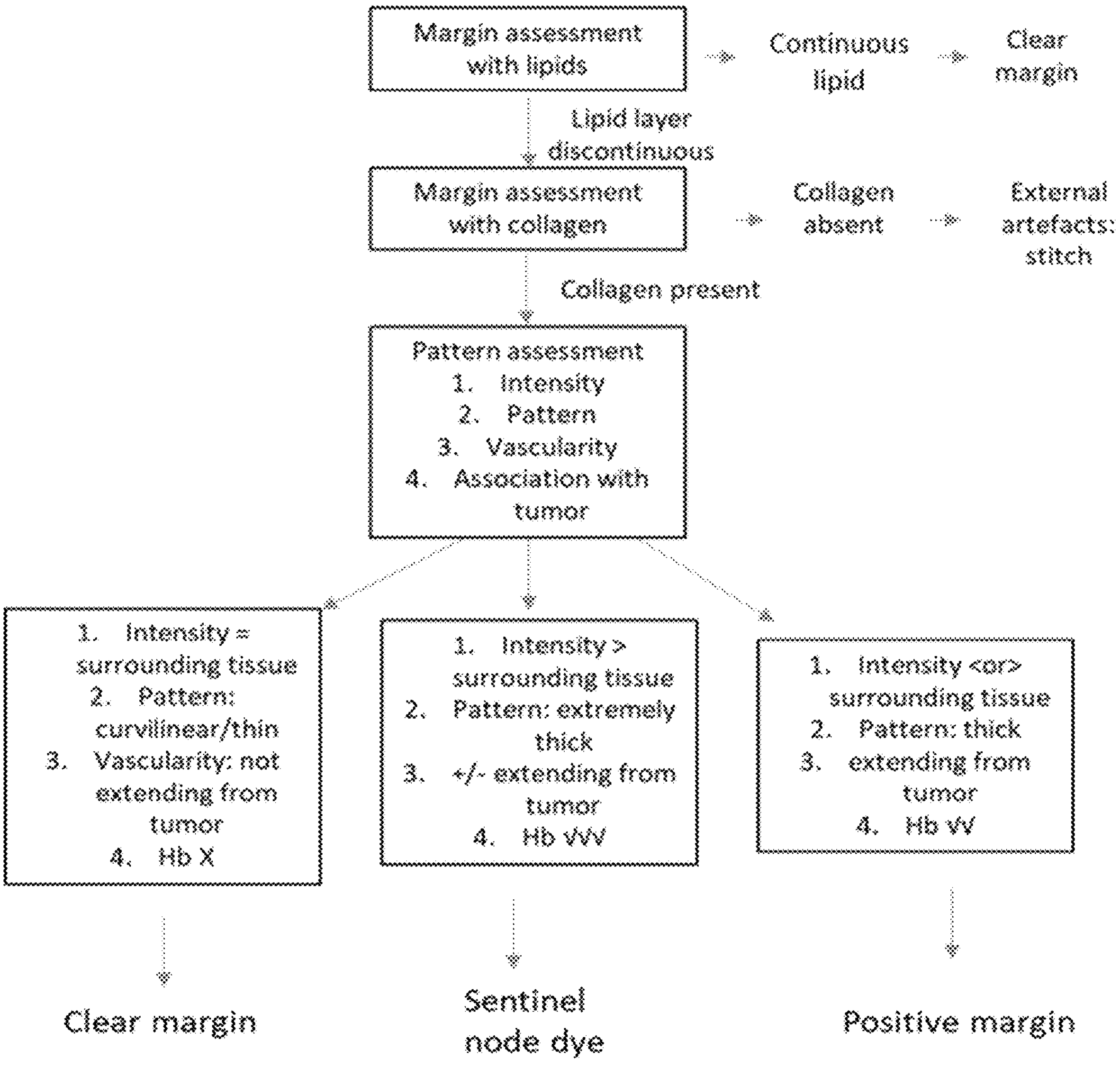
FIG. 2 shows the workflow for an ex vivo diagnosis flow chart using the present methods and system.
Figure 3:
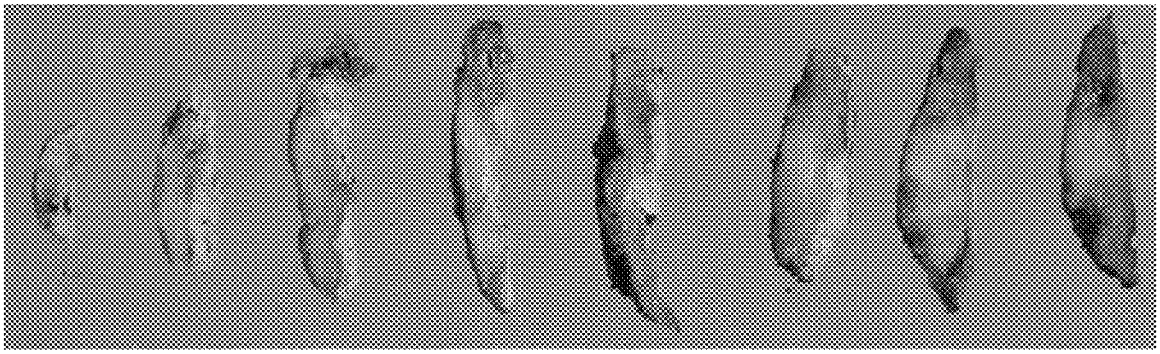
FIG. 3 shows cut sections of tissue specimen arranged from left to right (slice 1 to 8) showing fibro-fatty tissue with patchy areas of fibrosis. Representative slices of 3, 7 and 8 were selected for illustrations in FIGS. 4, 5 and 6, respectively.

The present methods and system advantageously help to screen tumor margins rapidly (in 20 minutes or less) post surgery using both high resolution ultrasound and photoacoustic images. From the photoacoustic images, lipid, collagen and hemoglobin may be identified and/or their pattern and distribution may be observed. The present methods and system significantly help in the reducing re-operative rates for the tumor patients. A diagnosis flow of the methods are shown in FIG. 2.

Figure 7A:
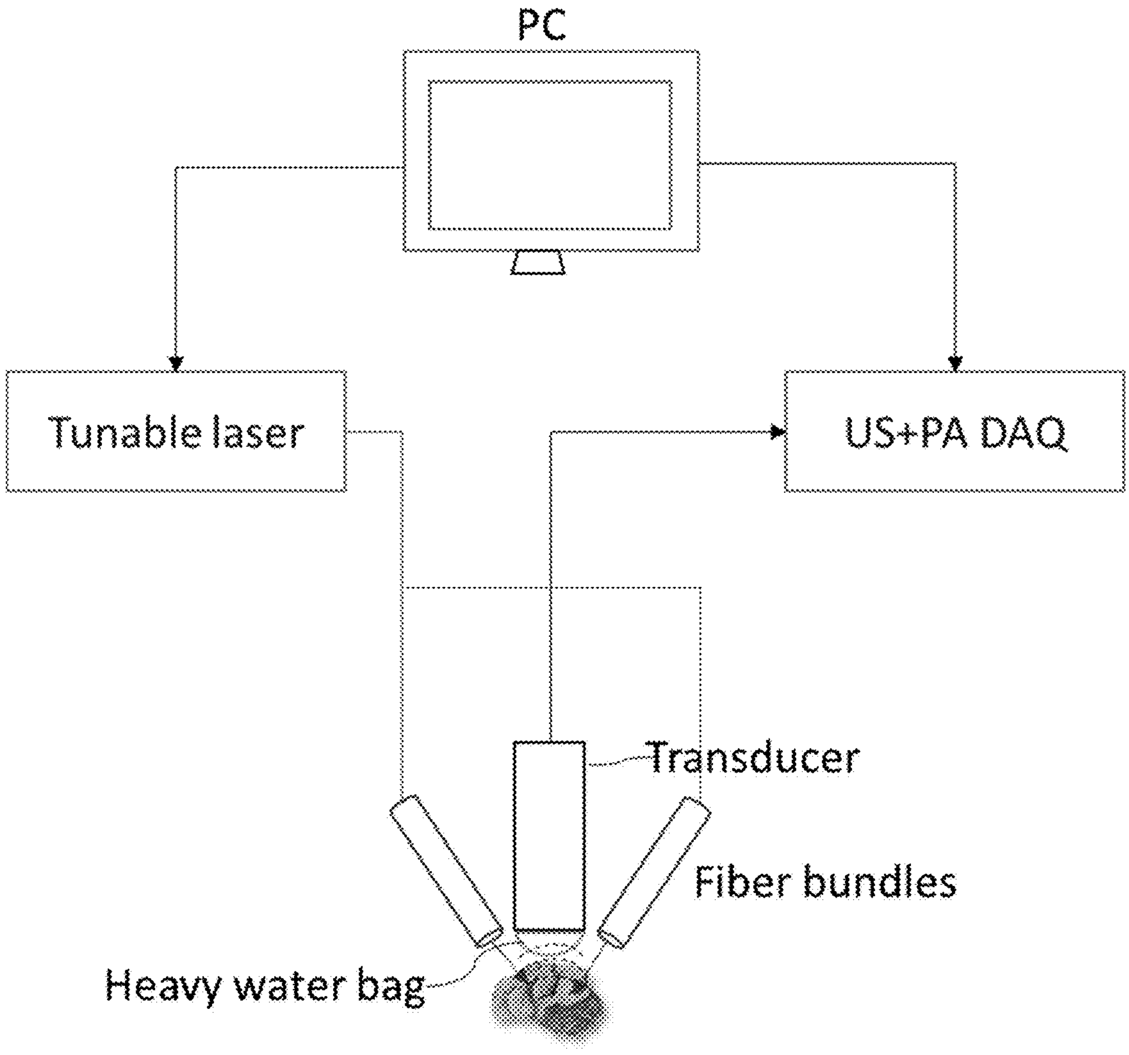
FIG. 7A is a general schematic of the present system, showing the US-PA dual frequency probe filled with heavy water for in vivo imaging. In other words, the probe is configured with a compartment filled with heavy water or one end of the probe that is to be placed proximal to a sample is applied with heavy water. US and PA denote for ultrasound and photoacoustic, respectively. DAQ denotes for the data acquisition module.
Figure 7B:
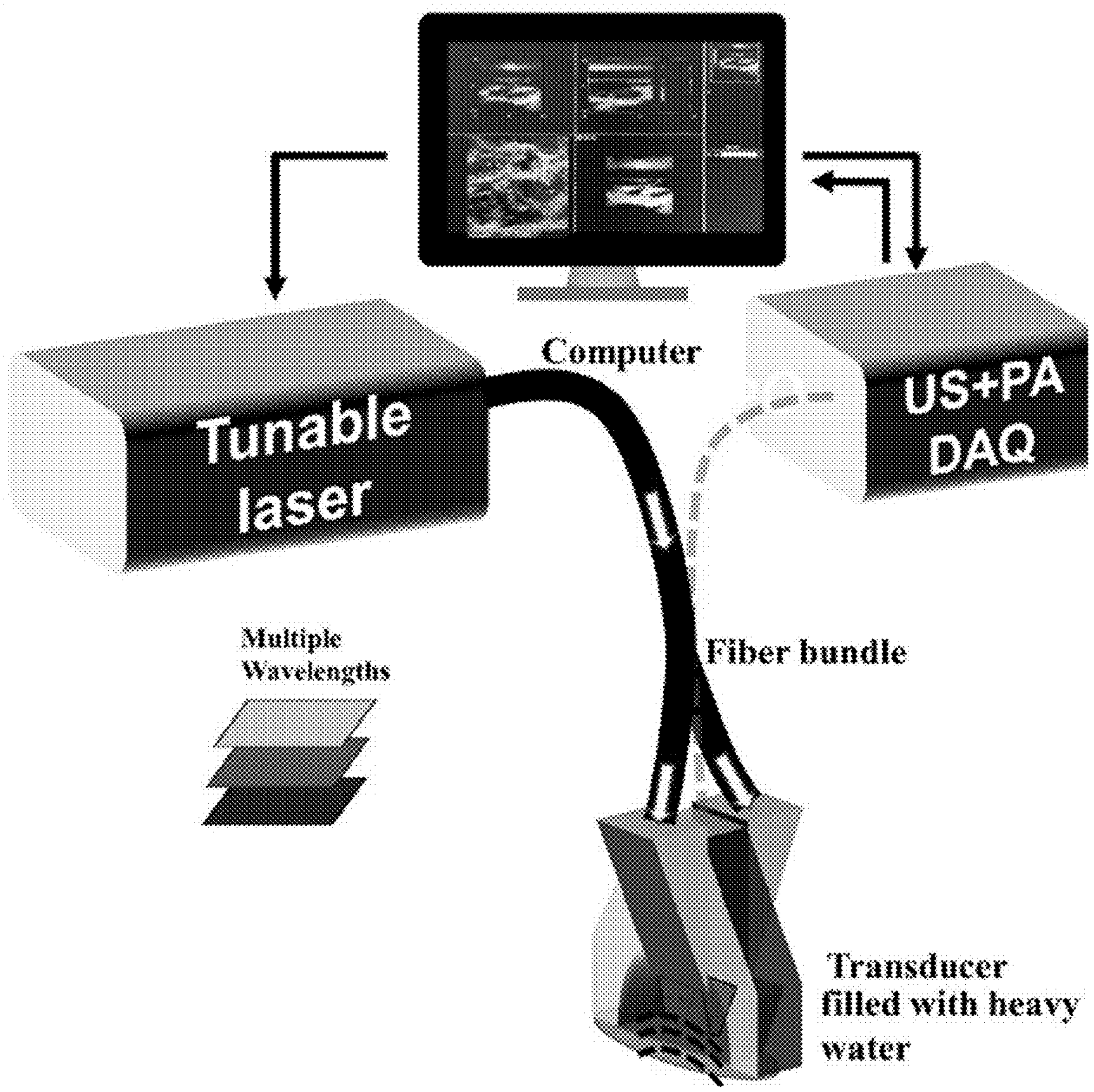
FIG. 7B is a general schematic of the present system, showing the US-PA dual frequency probe filled with heavy water for in vivo imaging. In other words, the probe is configured with a compartment filled with heavy water or one end of the probe that is to be placed proximal to a sample is applied with heavy water. US and PA denote for ultrasound and photoacoustic, respectively. DAQ denotes for the data acquisition module.
Figure 8:
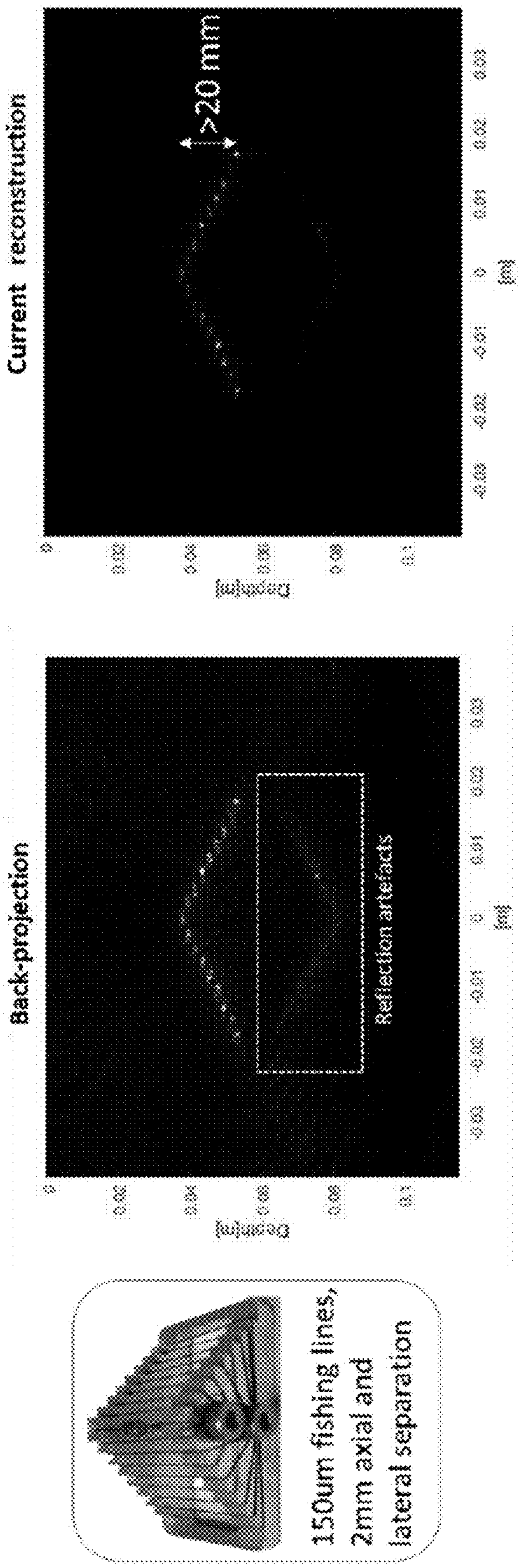
FIG. 8 shows phantom imaging using the presently developed US-PA imaging system. A pyramid shape phantom was imaged and reconstructed using a presently developed algorithm. Advantageously, a lot of noise was removed and the image can be rendered sharper than using a traditional back-projection algorithm. Also, an imaging depth of 20 mm or more was achieved.

Example 2: Description of Another Non-Limiting Example of the Present System Another non-limiting example of the hybrid ultrasound and photoacoustic (PA) imaging system is shown in FIGS. 7A and 7B for in vivo applications. This system is identical to the system described in example 1, except that the probe has a minor difference. All the components, such as the pulsed laser source for PA stimulation, the ultrasound and PA DAQ module, and the computer to control all the components, can be the same. However, for in vivo applications and in this instance, the probe is configured with a compartment that is filled or coated with heavy water, wherein the compartment has a surface comprised of a polyethylene membrane defining the front of the probe for optical transmission and acoustic detection. In another example, the compartment may be defined by one end of the probe that is to be placed proximal to a sample and having that end encapsulated with a polyethylene membrane, wherein the compartment can be filled or coated with heavy water.

Figure 9:
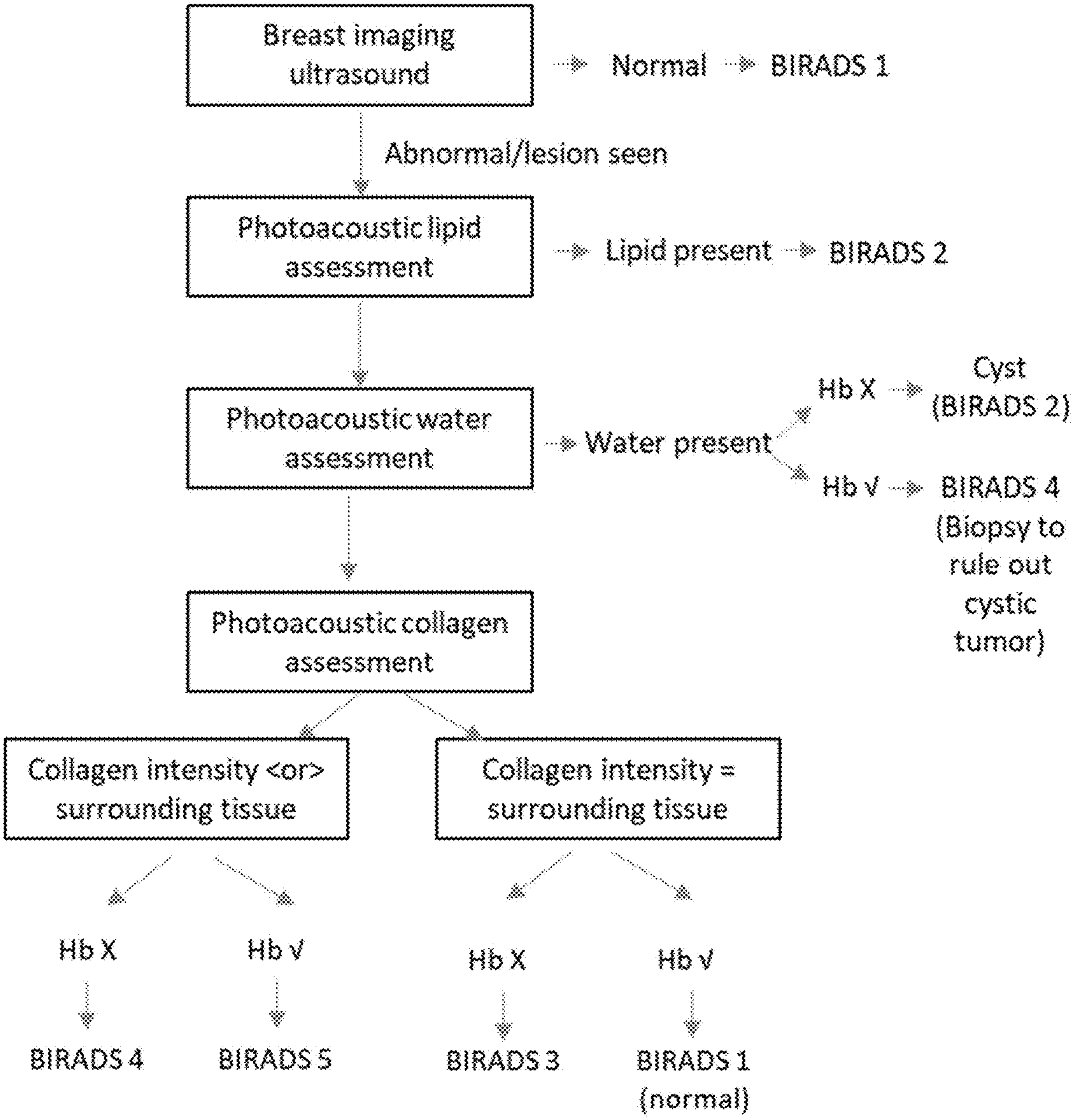
FIG. 9 shows the workflow for an in vivo diagnosis flow chart using the present methods and system. By going through this analysis chart, a clinician can screen out most of the benign tumors and save unnecessary biopsy operations. The method as illustrated in this workflow can be developed to be a decision table to assist clinicians. It can be developed into a fully automatic software to make diagnosis decisions too. The software uses the ultrasound and photoacoustic images so as to provide for diagnosis following the method illustrated in the flow chart.

In certain non-limiting instances, such as ex vivo applications, the probe may be mounted on a stage movable to have the probe positioned at different locations of a sample. In certain non-limiting instances, such as in vivo applications, the probe may be held by hand. The present system helps to screen benign tumors from suspected malignant tumor using both high resolution ultrasound and photoacoustic images, wherein lipid, collagen and haemoglobin can be identified using the photoacoustic images. The present system, and hence methods, significantly help in the reducing biopsy rates for the benign tumor patients. The diagnosis flow is shown in FIG. 9.

Example 3: Further Embodiments of the Present Methods and System

In various or certain non-limiting embodiments, both ultrasound imaging and photoacoustic imaging may be operable using the same transducing elements. The transducing elements operable to generate ultrasound imaging may be referred to as "transducer" in the present disclosure. Said differently, the transducer and transducing elements mentioned in the present disclosure may be the same. In non-limiting instances, the transducing elements for ultrasound imaging may operably emit ultrasound and receive ultrasound, while for photoacoustic imaging, the transducing elements may only receive ultrasound signals generated by the pulsed laser but may not emit ultrasound.

Also, the transducing elements mentioned in one or more examples of the present disclosure may be the same, and in such instances, the transducing elements for transmitting (and collecting) ultrasound signals and the transducing elements for collecting photoacoustic signals may be operated at different times (e.g. carried out sequentially without overlapping). In certain non-limiting examples, there is a center array (e.g. having a planar surface and/or containing 128 transducing elements) operable for both ultrasound (transmit and/or collect ultrasound signals) and photoacoustic (collect photoacoustic signals) imaging. In such example, there is another array having a curved surface (i.e. arc) having the transducing elements (e.g. containing 128 transducing elements) arranged thereon, wherein the transducing elements on the curved surface may be operable only to collect photoacoustic signals. In various non-limiting instances, the center array and one or more adjacent arrays may be constructed of different materials where the center array may be configured efficiently for both transmission and collection of ultrasound and photoacoustic signals while the adjacent array (e.g. having curved surface) may be configured efficiently only for receiving photoacoustic signals. In various non-limiting instances, the center array and one or more adjacent arrays may be operable at different frequencies, wherein the center array contains transducing elements operable at higher frequency compared to the transducing elements on the one or more adjacent arrays.

In various embodiments, any suitable ultrasound transducing elements can be used, i.e. there may be no restriction or specific requirement. In certain non-limiting embodiments, the transducing elements may be configured as an array, for example, having a higher frequency linear array (for ultrasound and/or PA imaging) of transducing elements and two arc segments of lower frequency transducing elements (for PA imaging only), to achieve better results. In any case, any kind of transducing elements operable under such configuration can be used. The term "linear array" interchangeably refers to an array having the planar surface. The term "arc segment" interchangeably refer to an array having the curved surface. In various embodiments, the planar surface or the curved surface may comprise 64 to 512 (e.g. 64 to 128, 64 to 256, 128 to 512, 264 to 512) transducing elements arranged thereon.

In various or certain non-limiting embodiments, the resolution and imaging depth in ultrasound and photoacoustic imaging may depend on the transducing elements operable frequency. In various or certain non-limiting instances, high frequency transducing elements are used to generate high resolution ultrasound images to track smaller tumors. Also, a combination of transducing elements may be involved for photoacoustic imaging to have a better imaging depth in photoacoustics, wherein some of the transducing elements are operable at such high frequency and some of the transducing elements are operable at a lower frequency to have better imaging depth from photoacoustics.

Figure 10A:
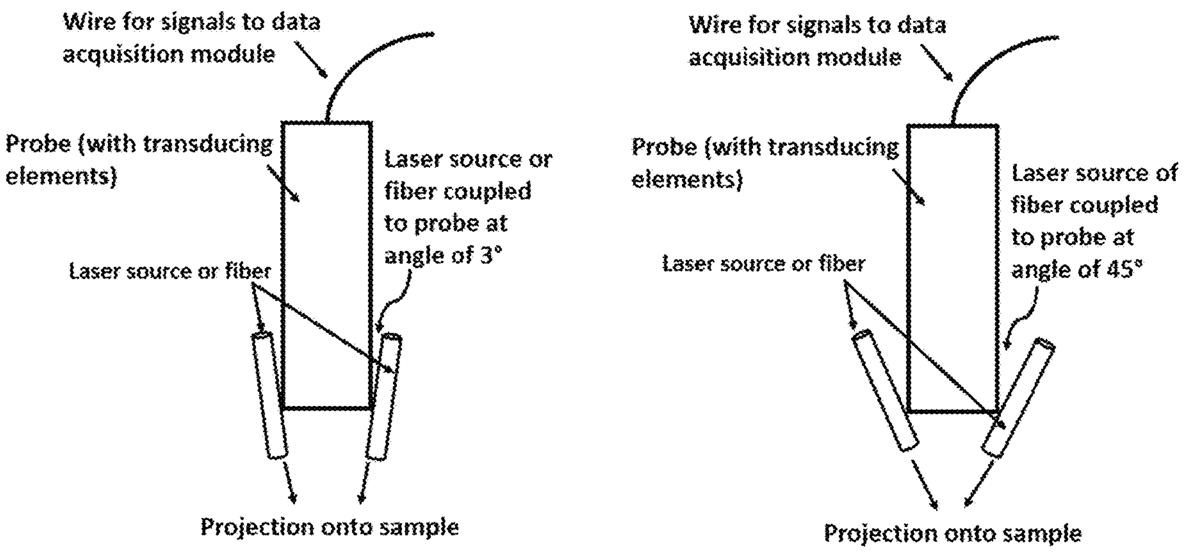
FIG. 10A shows two examples of schematic illustration of fiber or laser source configuration to the probe.
Figure 10B:
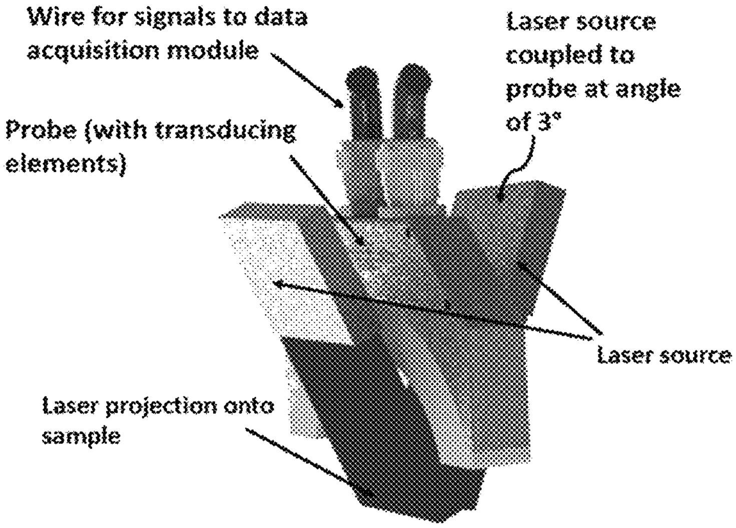
FIG. 10B shows an example of a three dimensional (3D) drawing of a laser source configuration to the probe. From the figures above, it can be seen that the lasers exit from the laser source or fiber to be projected onto the subject or sample to stimulate ultrasound and/or photoacoustic signals. Then the ultrasound and/or photoacoustic signals may be detected by the respective transducing elements. The laser may or may not be channeled into the probe directly.

In certain non-limiting embodiments, the probe may include one or more high frequency transducing elements arranged at the center of the array, wherein such transducing elements are operable for ultrasound imaging. In such non-limiting embodiments, low frequency transducing elements may be arranged on one or both sides of the high frequency transducing elements. A combination of the high and low frequency transducing elements may be operable for photoacoustic imaging. However, it may be noted that the probe (incorporated or integrated with the transducing elements) can have transducing elements all operable at the same frequency or some transducing elements operable at a higher frequency and some transducing elements operable at a lower frequency. In any case, both instances work for the system and methods of the present disclosure. FIG. 10A is intended as an example, which is meant to be non-limiting, for illustrating the angle of arrangement between a fiber (or laser source) and the probe so as to provide a better understanding.

In various embodiments, the transducing elements may be arranged in an array on a planar or curved surface. Each transducing element may be considered as corresponding to formation of one line in an image. More elements may provide a wider field-of-view and more precise image, but may incur more operational and computational costs.

In various embodiments and statements described above, the frequency used for ultrasound and photoacoustic imaging may not be the same or may be the same. As a non-limiting example, the transducing elements operating at the higher frequency (i.e. high frequency transducing elements) described in various embodiments and examples above may be operable at 5 to 15 Hz. For instance, the transducing elements arranged on the planar surface (i.e. linear array) may be operable at 5 to 15 Hz while the transducing elements arranged on the curved surface (i.e. arc segment) may be operable at 1 to 10 Hz. Another non-limiting example may be that the transducing elements arranged on both planar and curved surfaces as described in certain non-limiting embodiments and examples above are operable at the same frequency (e.g. 1 to 20 Hz). In one or more non-limiting examples, the transducing elements arranged on both planar and curved surfaces are operated at different times.

In various embodiments, there may be one or more fibers attached to the probe from the laser source. The one or more fibers may each be an optical fiber. The one or more fibers may be used to channel the laser from the laser source to the probe. The one or more fibers may be attached at an angle to the probe in certain non-limiting instances. If the one or more fibers are not attached at an angle, the laser or light may not be efficiently/properly delivered into probe and onto the sample. The one or more fibers may be attached to the probe at angle of 3 to 45 degree to illuminate an area of interest on the sample and/or to match the focal plane of the transducing element(s).

Example 4: Commercial and Potential Applications

The present disclosure introduces a system and methods for distinguishing benign and malignant breast tumor, including screening out benign tumor, which helps channel the suspected malignant tumor for biopsy confirmation. Currently in Singapore, about 75% biopsy of breast tumor are benign, which is a heavy burden for the healthcare system. By applying the present methods, the benign rate of biopsy can be reduced to be about 35% while maintaining the same sensitivity, based on preliminary data on ex vivo tumor samples. The present system and methods also help to screen tumor margins rapidly (in 20 minutes or less) post surgery. This significantly helps in the reducing re-operative rates for the tumor patients.

In the present disclosure, the concept/application of dual frequency for tracking smaller tumors, involving high frequency ultrasound, is introduced. The scanner (i.e. probe) provides cross-sectional 2D photoacoustic images with a user defined effective field-of-view (FOV) of 20 mm to 40 mm and wider scanning range. The switchable system of the present disclosure can be used for both ex vivo and in vivo imaging applications. From the intrinsic chromophores (lipid, blood, collagen, etc.) as marker using the flow chart (FIG. 2—ex vivo diagnosis flow chart), positive margin can be clearly identified eliminating all other external factors that may be present in the specimen, such as dye and stitches in the case of ex vivo samples. From the blood, lipid and collagen signals, etc., in vivo assessment of breast, benign tumors can be differentiated from malignant ones and the diagnostic workflow for this is given in FIG. 9 (in vivo diagnosis flow chart).

The use of single high frequency transducing elements tends to be not sufficient for deep (2 cm or more) photoacoustic imaging applications. The present technology does not suffer such a limitation. The present technology involves a dual frequency approach with, for example a central frequency of 7.5 MHz with elementary pitch of 0.2 mm for ultrasound imaging, and combining it with a central frequency of 3 MHz with elementary pitch of 0.5 mm for wide field photoacoustic imaging.

In the present disclosure, in order to differentiate for intrinsic chromophores, illumination at multiple wavelengths at high energy can be involved. Traditionally, there are no commercially available laser technologies which provide high repetition rate (more than 1 kHz) and pulse energy (more than 100 mJ) for the current applications. Moreover, the present methods and system are capable of tracking smaller tumors using ultrasound and identifying intrinsic biomarkers using photoacoustic imaging in ex vivo tissue and a flow chart to exclude the interference from dye, stiches, needle, etc. to accurately assess the tumor margins in excised breast tissue. Similarly, in the context of in vivo imaging, the identified biomarkers are used to generate a diagnostic workflow for differentiating benign from malignant tumors and thus avoid unnecessary biopsies.

The present methods and system are able to identify positive margins due to signals from the fibroglandular tissue which is predominant in Asian women's breast compared to Caucasian women. Through the inclusion of identifying biomarkers such as collagen and hemoglobin and the flowchart analysis based on the distribution pattern of these biomarkers in the specimen, the present technology allows positive margins in ex vivo tissue to be identified.

The present methods and system allow for a method of differentiating cancerous tumor from benign tumor using the system mentioned above. For example, the system is operable for ex vivo assessment of a state of a tumor margin in a sample, wherein the state of the tumor margin may be negative, positive, or may include a dye. The dye may be a sentinel node dye. The sentinel node dye may be administered at a suitable stage, e.g. during preparation of sample prior to operating the system to generate the ultrasound and photoacoustic images.

Figure 4:
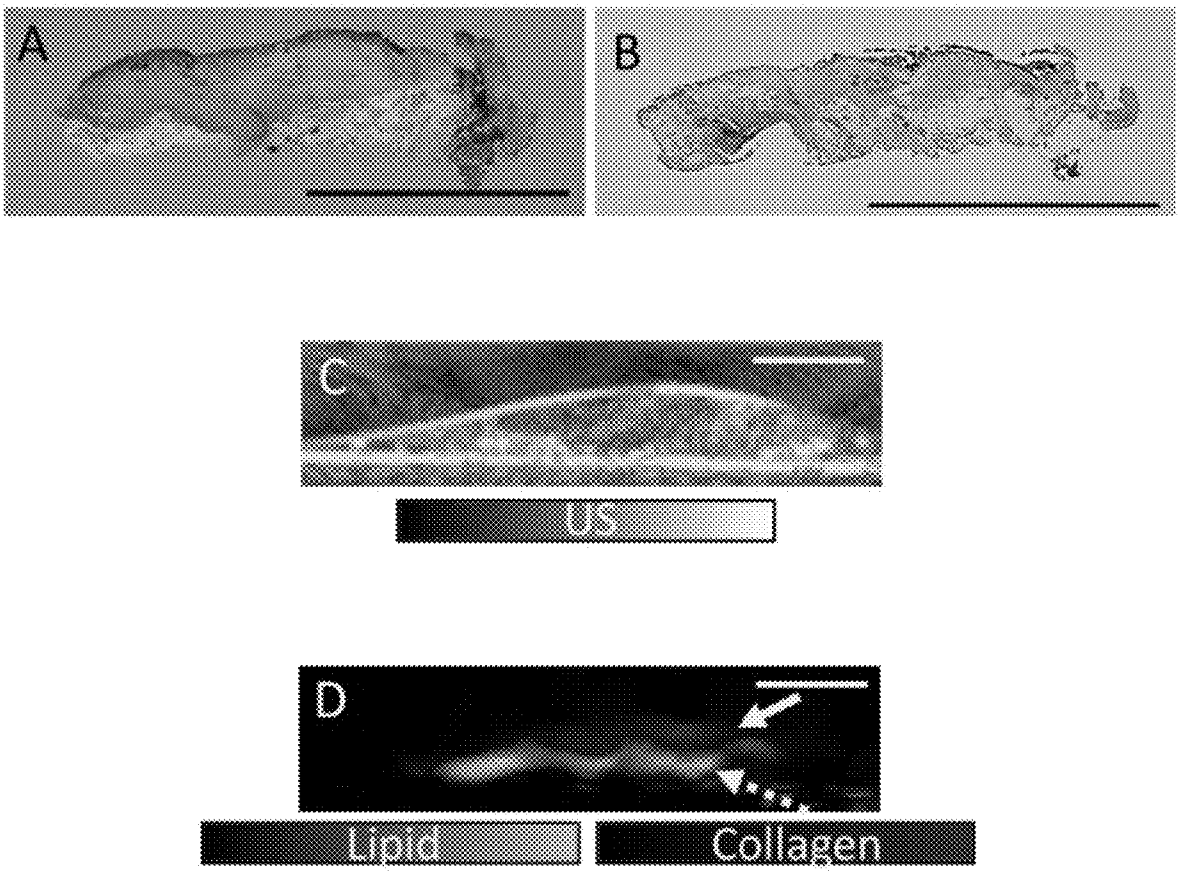
FIG. 4A shows a gross photo of slice 3 of the re-excision specimen, wherein the photo is obtained using a mobile phone. Scale bar denotes for 1 cm.
FIG. 4B shows a microscopic (low power whole slide view) image of slice 3 of the re-excision specimen. There are dense areas of fibrosis mainly in the top portions of the specimen (bold arrow) with scattered areas of fat in the inferior portions of the specimen (dotted arrow). Scale bar denotes for 1 cm.
FIG. 4C shows an ultrasound image of the excised tissue (slice 3) with histopathological correlation. Specifically.
FIG. 4D shows a photoacoustic image of the excised tissue (slice 3) with histopathological correlation. Specifically.
Figure 5:
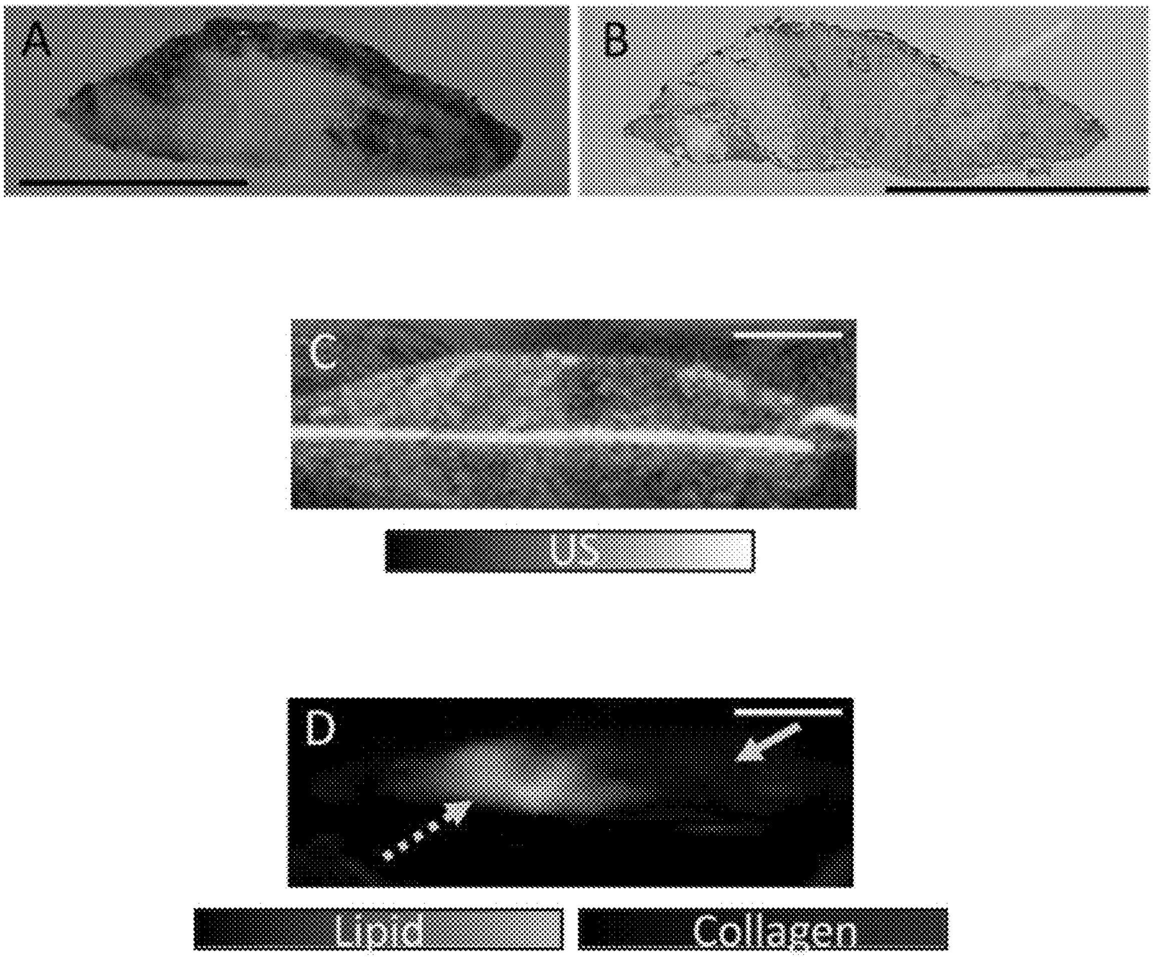
FIG. 5A shows a gross image of slice 7 of the re-excision specimen, wherein the photo is obtained using a mobile phone. Scale bar denotes for 1 cm.
FIG. 5B shows a microscopic (low power whole slide view) image of slice 7 of the re-excision specimen. There are dense areas of fibrosis mainly in the top portions of the specimen (bold arrow) with scattered areas of fat in the inferior portions of the specimen (dotted arrow). Scale bar denotes for 1 cm.
FIG. 5C shows an ultrasound image of the excised tissue (slice 7) with histopathological correlation. Specifically.
FIG. 5D shows a photoacoustic image of the excised tissue (slice 7) with histopathological correlation. Specifically.
Figure 6:
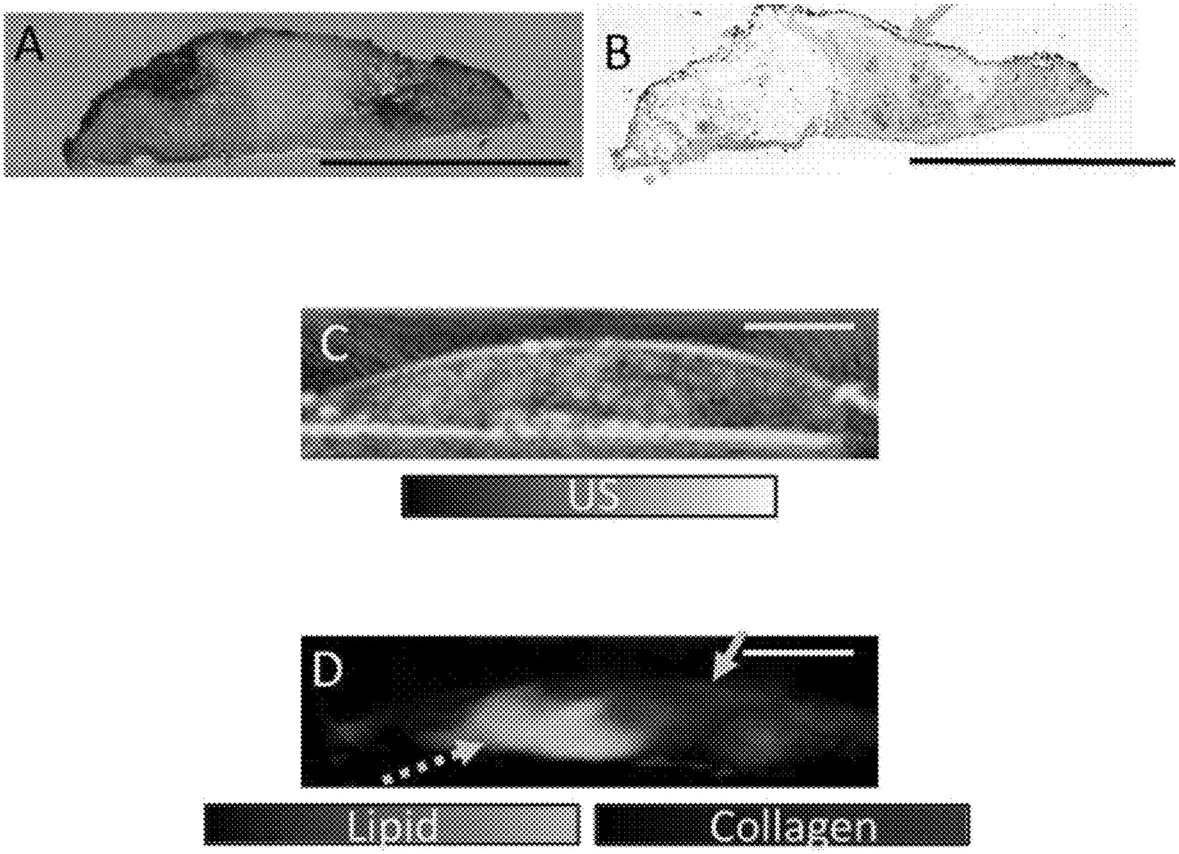
FIG. 6A shows a gross image of slice 8 of the re-excision specimen, wherein the photo is obtained using a mobile phone. Scale bar denotes for 1 cm.
FIG. 6B shows a microscopic (low power whole slide view) image of slice 8 of the re-excision specimen. There are patchy areas of fibrosis from the centre to the right of the specimen (bold arrow). Areas of fat can be seen in the left one-third of the specimen (dotted arrow). Scale bar denotes for 1 cm.
FIG. 6C shows an ultrasound image of the excised tissue (slice 8) with histopathological correlation. Specifically.
FIG. 6D shows a photoacoustic image of the excised tissue (slice 8) with histopathological correlation. Specifically.

In the present disclosure, the results obtained from the ultrasound and photoacoustic images from the ex vivo method can be correlated to a histopathological microscopy image. The histopathological microscopic image may be any microscopic image (e.g. see FIGS. 4A and 4B).

While the present disclosure has been particularly shown and described with reference to specific embodiments, it should be understood by those skilled in the art that various changes in form and detail may be made therein without departing from the spirit and scope of the present disclosure as defined by the appended claims. The scope of the present disclosure is thus indicated by the appended claims and all changes which come within the meaning and range of equivalency of the claims are therefore intended to be embraced.

The invention claimed is:

1. An ex vivo method of identifying a state of a tumor margin in a sample, the method comprising:

operating a system to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays, which is a linear array, comprises transducing elements arranged thereon which are operable at a frequency of 7 MHz to 10 MHz to transmit and collect ultrasound signals, and wherein one of the arrays, which is a linear array configured adjacent to a curved array, comprises dual-frequency transducing elements arranged thereon which are operable to collect photoacoustic signals, wherein the dual-frequency comprises a range of 2 MHz to 5 MHz and 7 MHz to 10 MHz;

and a data acquisition module which converts the ultrasound signals and the photoacoustic signals into the ultrasound image and the photoacoustic image, respectively, identifying from the photoacoustic image the presence or absence of lipids and observing for a pattern and distribution of the lipids, identifying from the photoacoustic image the presence or absence of collagen and observing for a pattern and distribution of the collagen;

identifying from the photoacoustic image the presence or absence of hemoglobin and observing for a pattern and distribution of the hemoglobin; and comparing from the photoacoustic image an intensity of the collagen, or collagen and hemoglobin with an intensity of tissue proximal to the collagen, or collagen and hemoglobin.

2. The ex vivo method of claim 1, wherein the state of the tumor margin is negative, positive, or comprises a dye.

3. The ex vivo method of claim 1, wherein operating the system comprises operating the laser source to generate the pulsed laser having:

a wavelength ranging from 600 nm to 2000 nm, a wave period of 10 ns or less, or a frequency of 1 to 100 Hz.

4. The ex vivo method of claim 1, wherein operating the system comprises having the laser source configured at an angle to the probe to deliver the pulsed laser to the sample, or having the laser source deliver the pulsed laser to the sample via a fiber, wherein one end of the fiber is configured at an angle to the probe.

5. The ex vivo method of claim 1, wherein operating the system comprises operating the probe in heavy water or having the probe incorporated with heavy water.

6. The ex vivo method of claim 1, wherein the arrays comprise one array having a planar surface configured between and adjacent to two arrays each having a curved surface, or wherein operating the system comprises operating transducing elements arranged on the planar surface at a higher frequency than or same frequency as transducing elements arranged on the curved surface.

7. The ex vivo method of claim 1, wherein observing for the pattern and distribution of the collagen further comprises observing the thickness of the collagen.

8. The ex vivo method of claim 1, further comprising:

observing the presence or absence of vascularity extension from a tumor; or observing for heterogeneity of the issue from the ultrasound image; or correlating the ultrasound image and the photoacoustic image to a histopathological microscopic image.

9. A method of determining a state of a tumor, the method comprising:

operating a system to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays, which is a linear array, comprises transducing elements arranged thereon which are operable at a frequency of 7 MHz to 10 MHz to transmit and collect ultrasound signals, and wherein one of the arrays, which is a linear array configured adjacent to a curved array, comprises dual-frequency transducing elements arranged thereon which are operable to collect photoacoustic signals, wherein the dual-frequency comprises a range of 2 MHz to 5 MHz and 7 MHz to 10 MHz; and a data acquisition module which converts the ultrasound signals and the photoacoustic signals into the ultrasound image and the photoacoustic image, respectively, identifying from the ultrasound image the presence or absence of an abnormal tissue or a lesion;

identifying from the photoacoustic image the presence or absence of lipids and observing for a pattern and distribution of the lipids, identifying from the photoacoustic image the presence or absence of water and observing for a pattern and distribution of the water;

identifying from the photoacoustic image the presence or absence of collagen and observing for a pattern and distribution of the collagen;

identifying from the photoacoustic image the presence or absence of hemoglobin and observing for a pattern and distribution of the hemoglobin; and comparing from the photoacoustic image an intensity of the collagen, or collagen and hemoglobin with an intensity of tissue proximal to the collagen, or collagen and hemoglobin.

10. The method of claim 9, wherein the state of the tumor is benign, malignant, or indeterminate.

11. The method of claim 9, wherein the tumor is a breast cancer tumor.

12. The method of claim 9, wherein operating the system comprises operating the laser source to generate the pulsed laser having:

a wavelength ranging from 600 nm to 2000 nm, a wave period of 10 ns or less, or a frequency of 1 to 100 Hz.

13. The method of claim 9, wherein operating the system comprises having the laser source configured at an angle to the probe to deliver the pulsed laser to the sample, or having the laser source deliver the pulsed laser to the sample via a fiber, wherein one end of the fiber is configured at an angle to the probe.

14. The method of claim 9, wherein operating the system comprises operating the probe in heavy water or having the probe incorporated with heavy water.

15. The method of claim 9, wherein the arrays comprise one array having a planar surface configured between and adjacent to two arrays each having a curved surface, or wherein operating the system comprises operating transducing elements arranged on the planar surface at a higher frequency than or same frequency as transducing elements arranged on the curved surface.

16. The method of claim 9, further comprising:

observing for heterogeneity of the tissue from the ultrasound image; or correlating the ultrasound image and the photoacoustic image to a histopathological microscopic image.

17. A system operable to generate an ultrasound image and a photoacoustic image, wherein the system comprises:

a probe configured to deliver a pulsed laser from a laser source to a sample, wherein the laser source is operable to generate the pulsed laser;

arrays coupled to the probe, wherein one of the arrays, which is a linear array, comprises transducing elements arranged thereon which are operable at a frequency of 7 MHz to 10 MHz to transmit and collect ultrasound signals, and wherein one of the arrays, which is a linear array configured adjacent to a curved array, comprises dual-frequency transducing elements arranged thereon which are operable to collect photoacoustic signals, wherein the dual-frequency comprises a range of 2 MHz to 5 MHz and 7 MHz to 10 MHz; and a data acquisition module which converts the ultrasound signals and the photoacoustic signals into the ultrasound image and the photoacoustic image, respectively.

18. The system of claim 17, wherein the laser source is configured at an angle to the probe to deliver the pulsed laser to the sample, or the laser source delivers the pulsed laser to the sample via a fiber, wherein one end of the fiber is configured at an angle to the probe.

19. The system of claim 17, wherein the probe is operable in heavy water or the probe is incorporated with heavy water.

20. The system of claim 17, wherein the arrays comprise one array having a planar surface configured between and adjacent to two arrays each having a curved surface, and/or wherein the transducing elements arranged on the planar surface are operable at a higher frequency than or same frequency as the transducing elements arranged on the curved surface.

* * * * *